United States Patent
Wang et al.

(10) Patent No.: US 8,780,165 B2
(45) Date of Patent: *Jul. 15, 2014

(54) PORTABLE REMOTE PRESENCE ROBOT

(75) Inventors: Yulun Wang, Goleta, CA (US); Charles S. Jordan, Santa Barbara, CA (US); Marco Pinter, Santa Barbara, CA (US); Daniel Steven Sanchez, Summerland, CA (US); Kevin Hanrahan, Santa Barbara, CA (US)

(73) Assignee: Intouch Technologies, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/549,971

(22) Filed: Jul. 16, 2012

(65) Prior Publication Data
US 2012/0281056 A1  Nov. 8, 2012

Related U.S. Application Data

(63) Continuation of application No. 12/548,122, filed on Aug. 26, 2009, now Pat. No. 8,384,755.

(51) Int. Cl.
*H04N 7/14* (2006.01)

(52) U.S. Cl.
CPC .................................. *H04N 7/14* (2013.01)

USPC ..................................... 348/14.05; 348/14.07

(58) Field of Classification Search
USPC ............ 348/14.01–14.09, 14.1, 14.11, 14.12; 709/203, 204; 700/13, 90, 245; 901/14, 901/19, 46
See application file for complete search history.

(56) References Cited

U.S. PATENT DOCUMENTS

| | | | |
|---|---|---|---|
| 2006/0082642 A1* | 4/2006 | Wang et al. ................ | 348/14.05 |
| 2007/0064092 A1* | 3/2007 | Sandbeg et al. ............ | 348/14.02 |

* cited by examiner

*Primary Examiner* — Tuan D Nguyen
(74) *Attorney, Agent, or Firm* — Chris Lambrecht

(57) ABSTRACT

A tele-presence system that includes a portable robot face coupled to a remote station. The robot face includes a robot monitor, a robot camera, a robot speaker and a robot microphone. The remote station includes a station monitor, a station camera, a station speaker and a station microphone. The portable robot face can be attached to a platform mounted to the ceiling of an ambulance. The portable robot face can be used by a physician at the remote station to provide remote medical consultation. When the patient is moved from the ambulance the portable robot face can be detached from the platform and moved with the patient.

5 Claims, 5 Drawing Sheets

PORTABLE REMOTE PRESENCE ROBOT

CROSS-REFERENCE TO RELATED APPLICATION

This is a continuation of U.S. application Ser. No. 12/548,122 filed Aug. 26, 2009.

BACKGROUND OF THE INVENTION

1. Field of the Invention

The subject matter disclosed generally relates to the field of robotic tele-presence systems.

2. Background Information

Robots have been used in a variety of applications. For example, robots have been used in manufacturing facilities, bomb detection/detonation, medical facilities, etc. The assignee of the present application has developed a tele-presence robot that includes a robot that is remotely controlled through a remote control station. The system is marketed under the product name RP-7. Both the robot and the remote station include cameras, monitors, microphones and speakers to allow for two audio-visual communication. The remote station also includes a joystick that can be operated by the user to move the robot and a robot head.

BRIEF SUMMARY OF THE INVENTION

A tele-presence system that includes a portable robot face coupled to a remote station. The robot face includes a robot monitor, a robot camera, a robot speaker and a robot microphone. The remote station includes a station monitor, a station camera, a station speaker and a station microphone.

DETAILED DESCRIPTION

Disclosed is a tele-presence system that includes a portable robot face coupled to a remote station. The robot face includes a robot monitor, a robot camera, a robot speaker and a robot microphone. The remote station includes a station monitor, a station camera, a station speaker and a station microphone. The portable robot face can be attached to a platform mounted to the ceiling of an ambulance. The portable robot face can be used by a physician at the remote station to provide remote medical consultation. When the patient is moved from the ambulance the portable robot face can be detached from the platform and moved with the patient.

Figure 1:
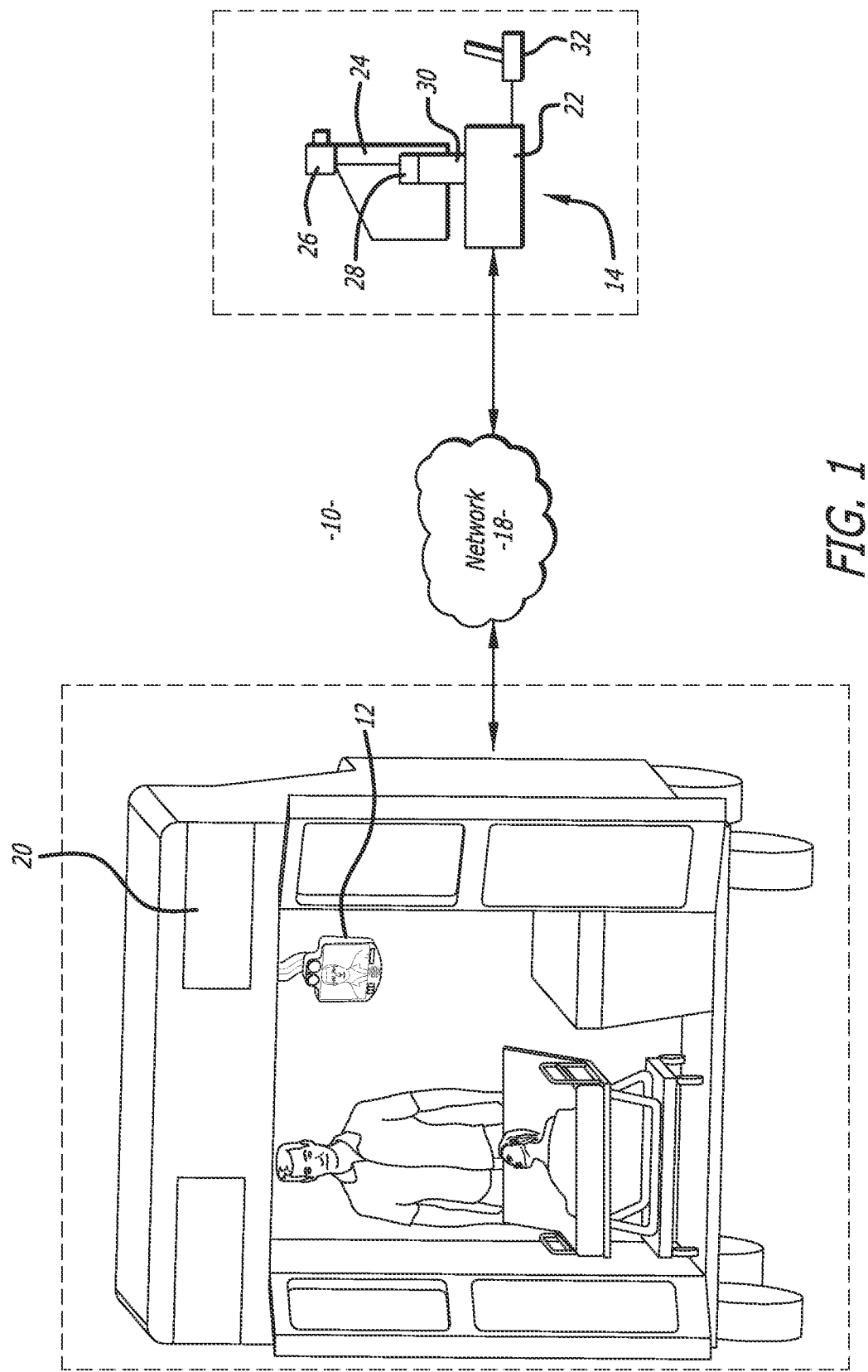
FIG. 1 is an illustration of a tele-presence system that includes a remote station coupled to a portable robot face located within an ambulance.

Referring to the drawings more particularly by reference numbers, FIG. 1 shows a tele-presence system 10. The system 10 includes a portable robot face 12 that is coupled to a remote control station 14 through a wireless network 18. The wireless network may be a cellular broadband network and/or a WiFi network. The portable robot face 12 is located within an ambulance 20.

The remote control station 14 may include a computer 22 that has a monitor 24, a camera 26, a microphone 28 and a speaker 30. The computer 22 may also contain an input device 32 such as a joystick or a mouse. The control station 14 is typically located in a place that is remote from the robot face 12. Although only one remote control station 14 is shown, the system 10 may include a plurality of remote stations 14. In general any number of robot faces 12 may be coupled to any number of remote stations 14 or other robot faces 12. For example, one remote station 14 may be coupled to a plurality of robot faces 12, or one robot face 12 may be coupled to a plurality of remote stations 14, or a plurality of robot faces 12. The system may include an arbitrator (not shown) that controls access between the robot face(s) 12 and the remote stations 14.

Figure 2:
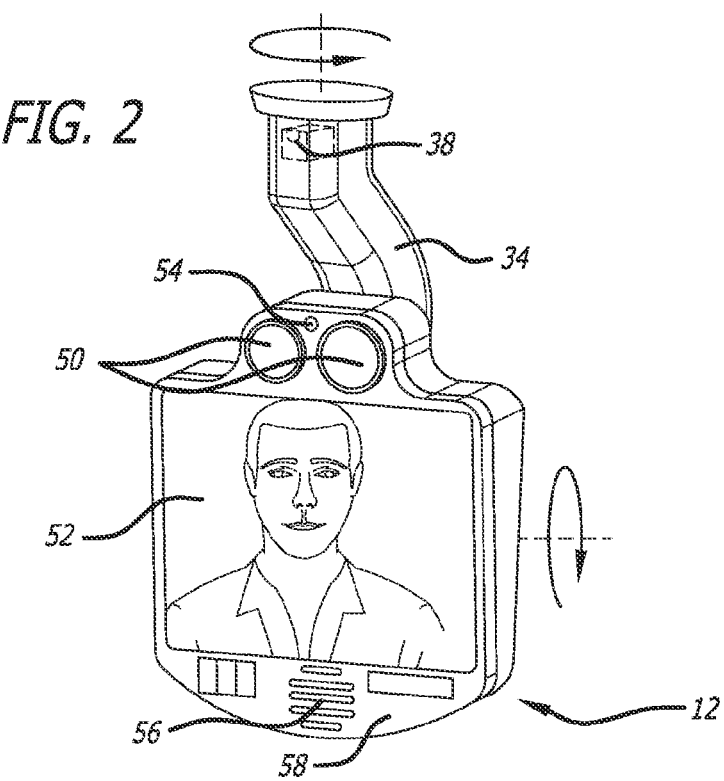
FIG. 2 is an illustration showing the portable robot face within the ambulance.
Figure 3:
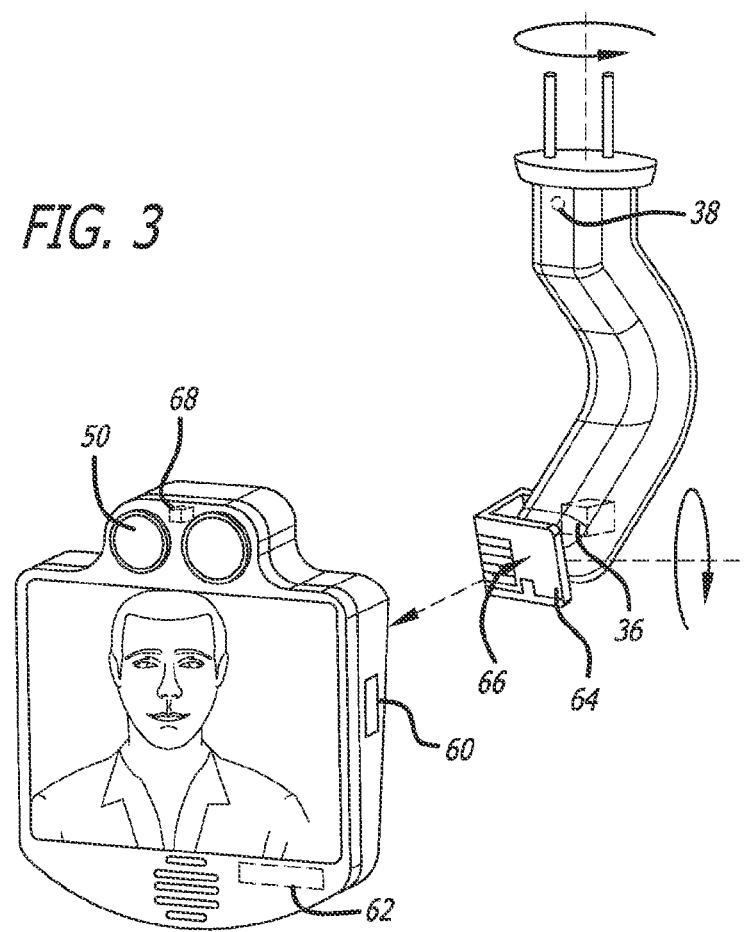
FIG. 3 is an illustration showing the portable robot face detached from a platform mounted to the ambulance ceiling.

As shown in FIGS. 2 and 3, the portable robot face 12 may be attached to a platform 34. The platform 34 may extend from the ceiling (not shown) of the ambulance 20. The platform 34 may include articulate joints 36 and 38 that provide at least two degrees of freedom and allow a user to move the robot face 12 to different positions to view a patient and an EMT within the ambulance.

Each robot face 12 includes a camera(s) 50, a monitor 52, a microphone(s) 54 and a speaker(s) 56 that are all attached to a housing 58. The robot camera 50 is coupled to the remote monitor 24 so that a user at the remote station 14 can view the patient and/or EMT. Likewise, the robot monitor 52 is coupled to the remote camera 26 so the patient and EMT may view the user of the remote station 14. The microphones 28 and 54, and speakers 30 and 56, allow for audible communication between the system operator and the patient and/or EMT.

The system 10 allows a system user such as a physician to view a patient in the ambulance and provide remote medical consultation through the remote station 14 and the robot face 12. Personnel such as the EMT can transmit questions and responses through the system back to the physician. The robot camera 50 allows the physician to view the patient and enhance the medical consultation. The robot monitor 52 can display the physician to provide a feeling of presence in the ambulance. The platform 34 allows the physician to pan and tilt the robot face 12.

The robot face 12 may include a wireless transceiver 60 that is coupled to the wireless network. The portable face 12 also includes a battery 62.

The system 10 may have certain components and software that are the same or similar to a robotic system provided by the assignee InTouch-Health, Inc. of Santa Barbara, Calif. under the name RP-7 and embodies a system described in U.S. Pat. No. 6,925,357, which is hereby incorporated by reference.

As shown in FIG. 3, the portable robot face 12 can be detached from the platform 34. The robot face 12 and platform 34 may have mechanical connectors 64 that allow the face 12 to be readily attached and detached from the platform 34. Likewise, the robot face 12 and platform 34 may include electrical connectors 66. The ambulance may include a wireless transceiver (not shown) that can provide wireless communication to the remote station. The electrical connectors 66 provide an electrical connection between the robot face 12 and the ambulance wireless transceiver. The connectors 66 may also provide power to the robot face 12. Alternatively, the wireless transceiver 60 of the robot face 12 may be coupled to the remote station through the ambulance wireless transceiver. The robot face may include an actuator system 68 that can move the camera 50 in two degrees of freedom. This allows the operator to move the camera field of view even when the face 12 is detached from the platform 34.

Figure 4:
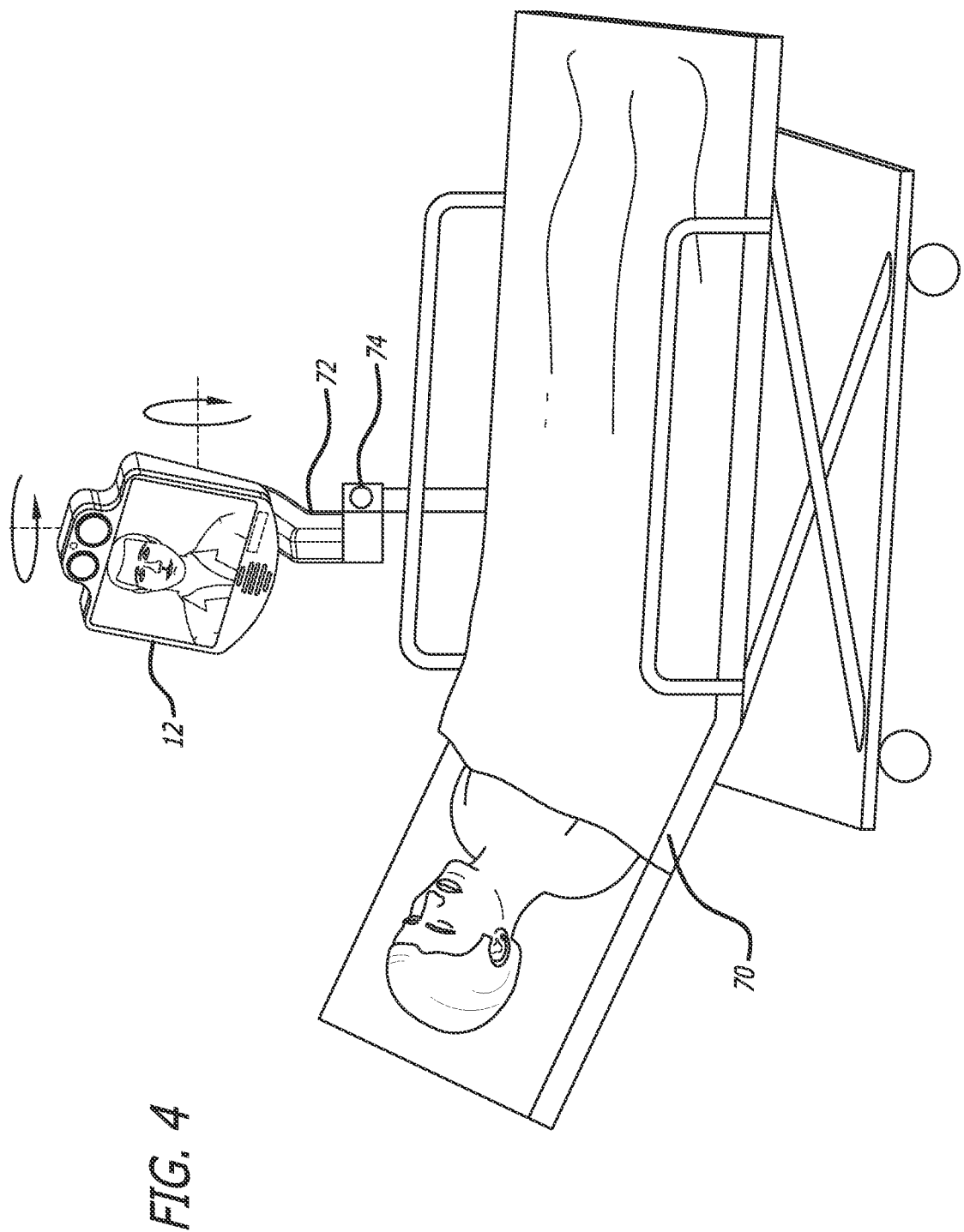
FIG. 4 is an illustration showing the portable robot face attached to a patient gurney.

As shown in FIG. 4 the portable robot face 12 can be detached from the platform (not shown) and attached to the patient gurney 70. The robot face 12 may be attached to a platform 72 with two degrees of freedom that allow the remote station user to move the robot face 12. The platform 72 may include a clamp 74 that allows for attachment to the gurney 70. The robot face 12 and patient can be moved out of the ambulance on the gurney 70. The portable aspect of the robot face 12 allows the face to be moved with the patient. The robot face 12 should be of a size and weight so that an individual can lift the face 12.

Figure 5:
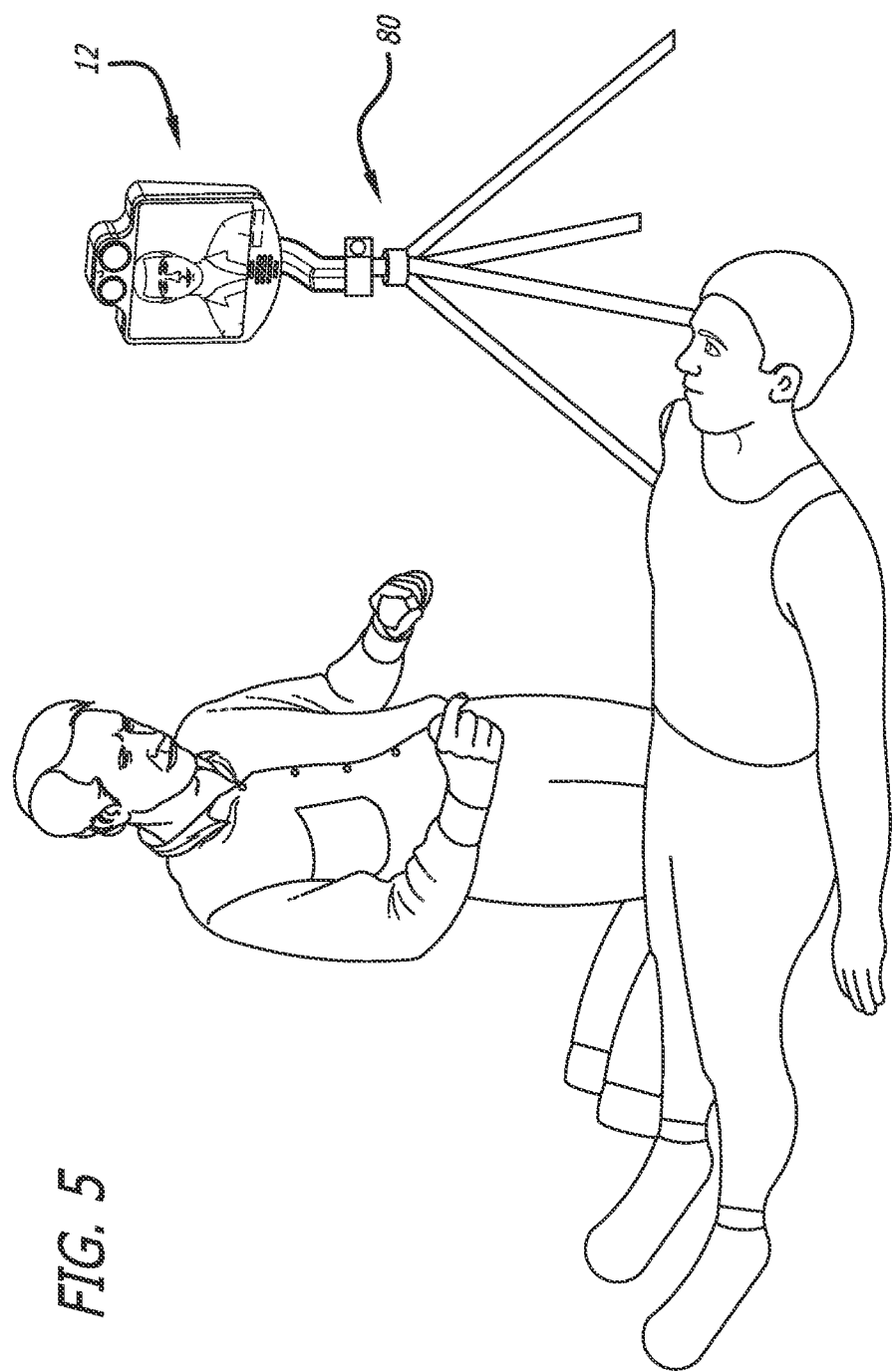
FIG. 5 is an illustration showing the portable robot face attached to a stand.

As shown in FIG. 5 the portable robot face 12 can be detached from the ambulance platform (not shown) and attached to a stand 80 at a remote location. The portable nature of the robot face 12 allows the face 12 to be taken to any location to allow for remote tele-presence of the operator of the remote station. If the operator is a physician the portable robot face 12 allows for remote medical consultation at any site.

Figure 6:
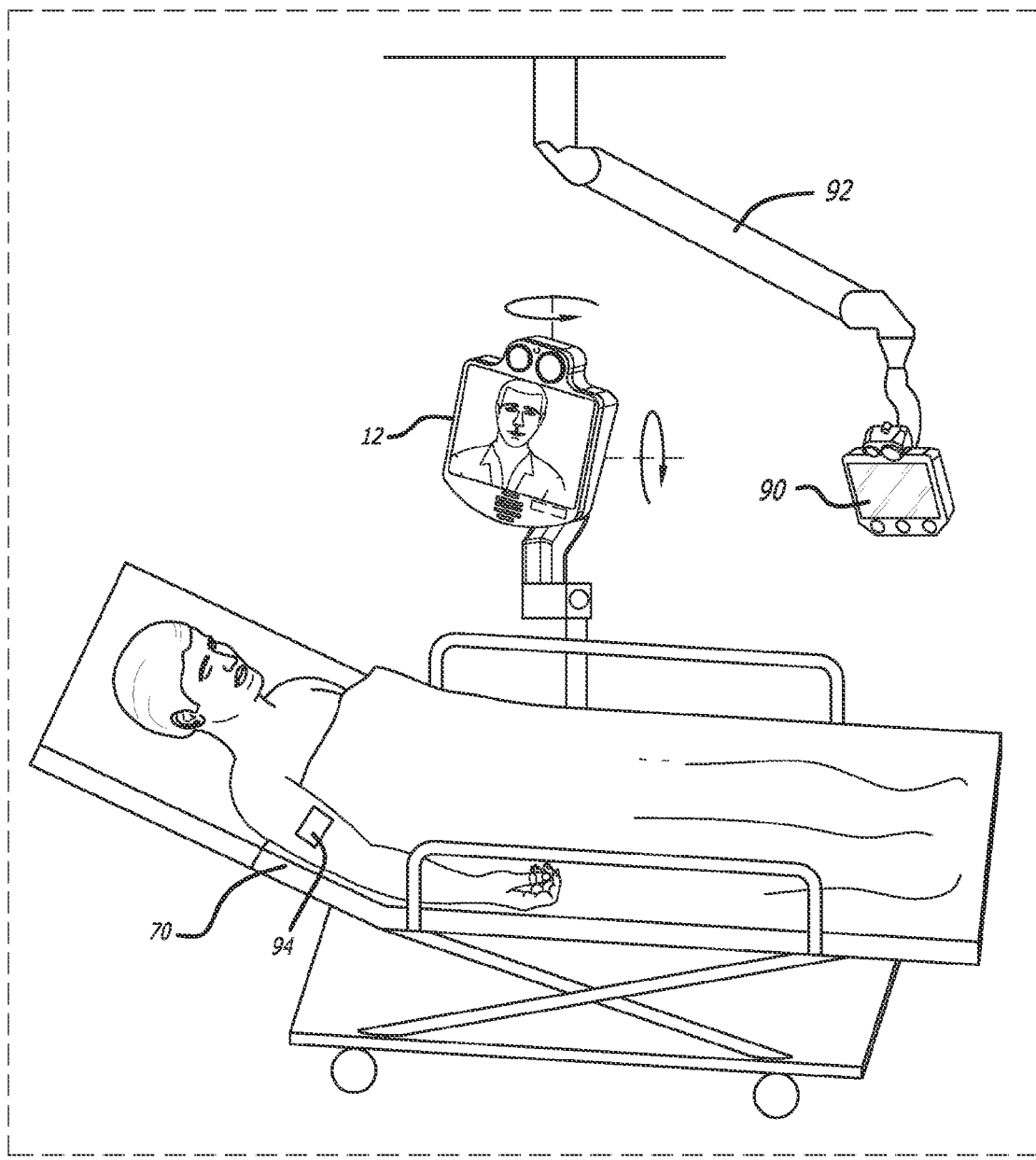
FIG. 6 is an illustration showing a patient within a healthcare facility that has a robot face attached to a boom.

FIG. 6 shows the patient and gurney moved into a healthcare facility with a robot face 90 attached to a boom 92. When the gurney 70 is moved into close proximity with the healthcare facility the robot face wireless transceiver may be coupled to the remote station thru the healthcare facility local wireless network such as a WiFi network. Once inside the facility the portable robot face can be connected to an electrical power outlet and a network for Ethernet connection. An electronic ID device 94 may be attached to the patient. The ID device 94 may transmit a wireless signal to the robot face 90 attached to the boom 92. Receipt of the signal by the face 90 may cause the remote station to be coupled to the robot face 90 attached to the boom 92 instead of the portable robot face 12. The robot face 90 may be coupled to the remote station by other means. For example, a nurse may type in information into the healthcare facility network system that identifies the new location of the patient. Such an entry may cause the system to switch the remote control station to the robot face 90. Additionally, there may be other methodologies for inducing the system to automatically transfer the remote station from one robot to another robot.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for providing a remote medical consultation, comprising:

capturing an image of a physician with a station camera of a remote station, the remote station includes a station monitor, a station speaker and a station microphone;

transmitting the physician image to a portable robot face mounted to a platform, the robot face including a robot monitor, a robot camera, a robot speaker and a robot microphone;

capturing an image of a patient with the robot camera;

transmitting the patient image to the remote station;

displaying the patient image on the station monitor of the remote station;

transmitting an audio command from the station microphone to the robot speaker;

detaching the portable robot face from the platform;

moving the patient and the portable robot to a new location; and displaying the physician image on the robot monitor while said portable robot face is detached from the platform.

2. The method of claim 1, wherein the platform is attached to an ambulance.

3. The method of claim 1, further comprising attaching the portable robot face to a patient gurney.

4. The method of claim 1, further comprising coupling the portable robot face to a healthcare facility network through a wireless transceiver of the portable robot face.

5. The method of claim 1, further comprising attaching a wireless identification device to the patient and moving the patient into a healthcare facility that includes a robot face attached to a boom, the robot face receives a wireless signal from the wireless identification device and the remote station becomes coupled to the robot face attached to the boom.

* * * * *